(12) United States Patent
Foguet Roca (10) Patent No.: US 11,540,981 B2
(45) Date of Patent: Jan. 3, 2023

(54) NANOEMULSION FORMULATION WITH IMPROVED STABILITY AND CELL PENETRATION

(75) Inventor: Montserrat Foguet Roca, Leverkusen (DE)

(73) Assignee: BIOFRONTERA BIOSCIENCE GMBH, Leverkusen (DE)

( * ) Notice: Subject to any disclaimer, the term of this patent is extended or adjusted under 35 U.S.C. 154(b) by 48 days.

(21) Appl. No.: 12/520,759

(22) PCT Filed: Dec. 21, 2007

(86) PCT No.: PCT/EP2007/011404
§ 371 (c)(1),
(2), (4) Date: Jun. 22, 2009

(87) PCT Pub. No.: WO2008/077641
PCT Pub. Date: Jul. 3, 2008

(65) Prior Publication Data
US 2009/0324727 A1    Dec. 31, 2009

(30) Foreign Application Priority Data
Dec. 22, 2006   (EP) ..................................... 06026698

(51) Int. Cl.
| | | |
|---|---|---|
| *A61K 47/10* | (2017.01) | |
| *A61K 9/107* | (2006.01) | |
| *A61P 17/02* | (2006.01) | |
| *A61K 8/06* | (2006.01) | |
| *A61K 8/55* | (2006.01) | |
| *A61Q 19/00* | (2006.01) | |
| *A61K 8/37* | (2006.01) | |
| *A61K 8/44* | (2006.01) | |
| *A61K 8/49* | (2006.01) | |
| *B82Y 5/00* | (2011.01) | |
| *A61K 8/34* | (2006.01) | |

(52) U.S. Cl.
CPC .................. *A61K 8/06* (2013.01); *A61K 8/34* (2013.01); *A61K 8/375* (2013.01); *A61K 8/44* (2013.01); *A61K 8/4993* (2013.01); *A61K 8/553* (2013.01); *A61K 9/107* (2013.01); *A61Q 19/00* (2013.01); *B82Y 5/00* (2013.01); *A61K 2800/21* (2013.01); *A61K 2800/413* (2013.01)

(58) Field of Classification Search
CPC . A61K 8/06; A61K 8/34; A61K 9/107; A61K 9/14; A61K 8/553; A61K 8/062; A61K 2800/413
See application file for complete search history.

(56) References Cited

U.S. PATENT DOCUMENTS

| | | |
|---|---|---|
| 5,891,490 A | 4/1999 | Merabet |
| 6,165,500 A * | 12/2000 | Cevc .............................. 424/450 |
| 6,245,349 B1 * | 6/2001 | Yiv ....................... A61K 9/1075 424/450 |
| 6,274,150 B1 | 8/2001 | Simonnet et al. |
| 6,375,960 B1 | 4/2002 | Simonnet et al. |
| 6,413,527 B1 | 7/2002 | Simonnet et al. |
| 6,500,862 B1 | 12/2002 | Zanello |
| 6,559,183 B1 * | 5/2003 | Schmid ................... A61P 35/00 514/561 |
| 6,602,511 B2 | 8/2003 | von Corswant |
| 6,897,238 B2 | 5/2005 | Anderson |
| 2002/0155084 A1 | 10/2002 | Roessler et al. |
| 2003/0167033 A1 | 9/2003 | Chen et al. |
| 2003/0190347 A1 * | 10/2003 | Supersaxo ........... A61K 9/4858 424/450 |
| 2005/0158389 A1 | 7/2005 | Domb |
| 2005/0208083 A1 | 9/2005 | Annis |

(Continued)

FOREIGN PATENT DOCUMENTS

| | | |
|---|---|---|
| EP | 0 620 271 A1 | 10/1994 |
| EP | 0 704 209 A1 | 9/1995 |

(Continued)

OTHER PUBLICATIONS

O'Neil, Maryadele J.; Heckelman, Patricia E.; Koch, Cherie B.; Roman, Kristin J.; Kenny Catherine, M.; D'Arecca, Maryann R. editors; "The Merck Index: An Encyclopedia of Chemicals, Drugs, and Biologicals," 2006; Merck & Co., Inc.; entries for "aminolevulinic acid," "Lecithins," and "Polysorbates" pp. 1-8 (as provided).*
International Food Information Service; "Dictionary of Food Science and Technology," 2nd ed. 2009, Wiley-Blackwell, p. 250.*
Tadros, Tharwat et al.; "Formation and stability of nano-emulsions," 2004, Elsevier, Advances in Colloid and Interface Science, vol. 108-109, pp. 303-318.*
Kang, Ki-Choon et al.; "Preparation and Characterization of Nano-Liposomes Using Phosphatidylcholine," 2005, Elsevier; International Journal of Industrial and Engineering Chemistry, vol. 11, No. 6, pp. 847-851.*

(Continued)

*Primary Examiner* — David J Blanchard
*Assistant Examiner* — Ivan A Greene
(74) *Attorney, Agent, or Firm* — Lathrop GPM LLP; James H. Velema, Esq.; Laura A. Labeots, Esq.

(57) ABSTRACT

The present invention relates to a nanoemulsion comprising at least one aqueous component and a carrier, wherein the carrier comprises at least one lipophilic component, at least one surfactant and at least one alcohol. The present invention further relates to a composition comprising said nanoemulsion and an active agent. In particular, the composition is present as a gel and the active agent is 5-aminolevulinic acid, a derivative, precursor and/or metabolite thereof. The invention further relates to the preparation of said nanoemulsion and/or composition and to their use for the treatment of dermatological diseases, virus-associated diseases as well as diseases associated with cell proliferation, in particular, tumor diseases and/or psoriasis. The present invention is further directed to the use of said nanoemulsion in cosmetics.

10 Claims, 6 Drawing Sheets

(56) References Cited

U.S. PATENT DOCUMENTS

| | | | |
|---|---|---|---|
| 2006/0078525 A1* | 4/2006 | Tomokuni | A61K 8/068 424/70.13 |
| 2006/0140984 A1 | 6/2006 | Tamarkin et al. | |
| 2011/0060042 A1 | 3/2011 | Ito | |

FOREIGN PATENT DOCUMENTS

| | | |
|---|---|---|
| EP | 1 473 367 A1 | 11/2004 |
| EP | 1 655 021 A1 | 5/2006 |
| JP | 2002-302414 A | 10/2002 |
| JP | 2006-273821 A | 10/2006 |
| WO | 96/41647 A1 | 12/1996 |
| WO | 97/41855 A1 | 11/1997 |
| WO | 98/21307 A1 | 5/1998 |
| WO | 2002/066589 A2 | 8/2002 |
| WO | 2005/027872 A2 | 3/2005 |
| WO | 2005/110370 A1 | 11/2005 |

OTHER PUBLICATIONS

Sarker, Dipak k.; "Engineering of Nanoemulions for Drug Delivery," 2005, Betham Science Ltd. Current Drug Delivery, vol. 2, No. 4, pp. 297-310.*

Aboofazeli, Reza et al.; "Particle Size Analysis of Concentrated Phospholipid Microemulsions: I. Total Intensity Light Scattering," 2000; AAPS Pharmsci, vol. 2, Issue 2, pp. 1-13.*

L'Alloret et al.; "Nanoemulsions: a new vehicle for skincare products," 2004, Elsevier, Advanced Colloid and Interface Science, vol. 108-109, pp. 145-149.*

Binks; "Phase Behaviour of microemulsions stabilised by double chain cationic surfactants and alcohol co-surfactants," 2003; Elsevier, Colloids and Surfaces A: Physicochem. Eng. Aspects, vol. 212, pp. 135-145.*

Sarker; "Engineering of Nanoemulsions for Drug Delivery," 2005, Current Drug Delivery, vol. 2, No. 4, pp. 297-310.*

Moreno ("Lecithin-Based Oil-in-Water Microemulsions for Parenteral Use: Pseudoternary Phase Diagrams, Characterization and Toxicity Studies," 2003, Wiley-Liss Journal of Pharmaceutical Science, vol. 92, No. 7, pp. 1428-1437.*

Yuan et al.; "Investigation of microemulsion system for transdermal delivery of meloxicam," Elsevier, 2006; International Journal of Pharmaceutics, vol. 321, pp. 117-123.*

Wang et al.; "Microemulsions as topical delivery vehicles for the anti-melanoma prodrug, temozolomide hexyl ester (TMZA-HE)," Jun. 2007; JPP, Journal of Pharmacy and Pharmacology, vol. 59, pp. 787-794.*

Binks; "Phase Behaviour of microemulsions stabilised by double chain cationic surfactants and alcohol co-surfactants," 2003; Elsevier, Colloids and Surfaces A: Physicochem. Eng. Aspects, vol. 212, pp. 135-145. (Year: 2003).*

Sarker; "Engineering of Nanoemulsions for Drug Delivery," 2005, Current Drug Delivery, vol. 2, No. 4, pp. 297-310. (Year: 2005).*

Sinko et al.; "Martin's Physical Pharmacy and Pharmaceutical Sciences, Physical Chemical and Biopharmaceutical Principles in the Pharmaceutical Sciences, 15th ed." 2009, Chapter 18, "Coarse Dispersions" pp. 499-530. (Year: 2009).*

PCT International Search Report for PCT/EP2007/014404 dated May 9, 2008 (4 pages).

Fritsch et al., "Fluorescence Diagnosis and Photodynamic Therapy of Skin Diseases," Atlas and Handbook, 2003, pp. 23-31.

Fendler, J.H. et al., "Liposomesas Drug Carriers." Life Sciences, 1977, pp. 1109-1120, vol. 20, No. 7, Pergamon Press.

Danielsson, I. et al., "The Definition of Microemulsion." Colloids and Surfaces, 1981, 3, pp. 391-392, Elsevier Scientific Publishing Company.

Aboofazeli, R. et al., "Particle Size Analysis of Concentrated Phospholipid Microemulsions: I. Total Intensity Light Scattering." AAPS Parmsci, 2000, pp. 1-13, 2(2), article 13.

Bagwe, R.P. et al., "Improved Drug Delivery Using Microemulsions: Rationale, Recent Progress, and New Horizons." Critical Reviews in Therapeutic Drug Carrier Systems, 2001, pp. 77-140, 18(1), Begell House, Inc.

Weiss, J. et al., "Nanostructured Encapsulation Systems: Food Antimicrobials." Global Issues in Food Science and Technology, 2009, Chapter 24, pp. 425-479, Elsevier Inc.

* cited by examiner

NANOEMULSION FORMULATION WITH IMPROVED STABILITY AND CELL PENETRATION

CROSS REFERENCES TO RELATED APPLICATIONS

This application claims the priority benefit of PCT/EP2007/011404 filed on Dec. 21, 2007 and European Application No. 06026698.8 filed on Dec. 21, 2006. The entire contents of these applications are hereby incorporated in their entirety.

BACKGROUND OF THE INVENTION

Nanoemulsions constitute a colloidal system. Colloidal systems include micelles, liposomes, virosomes, nanosuspensions, microemulsions and polymer solutions. Nanoemulsions, based on their physical and chemical characteristics, belong to the group of the microemulsions. Microemulsions are aqueous dispersions of homogeneous, micro-sized particles composed of a lipid core surrounded by surfactant and co-surfactant monolayers. Nanoemulsions are characterized by a mean particle size (mean diameter) of less than 200 nm, often less than 100 nm, and a narrow monodisperse particle size distribution. Further, nanoemulsions are transparent and slightly opalescent. They are generally manufactured by mechanical fragmentation of an oily phase in an aqueous phase in the presence of a surfactant. The very small size of the oily globules is often obtained by virtue of at least one pass through a high-pressure homogenizer or a sonicator. The preparation of the nanoemulsions described here does not require such high shear devices. The small size of the globules and their high homogeneity confers on them cosmetically advantageous properties which distinguish them from conventional emulsions: They are transparent and exhibit a novel texture. Further, they can carry active agents more efficiently and, thus, become increasingly important in the field of medicine and pharmacy.

Microemulsions, called nanodispersions, are known in the art which comprise a) a membrane-forming molecule, e.g. soy lecithin, b) a co-emulgator, c) a lipophilic component, e.g. caprylic and/or capric triglyceride (Miglyol 812 or Myritol 318) and, optionally, d) alcohol, in particular, ethanol (EP 0 956 853). These nanodispersions are used in pharmaceutical formulations as transport vehicle for pharmaceutically active agents.

However, the use of ethanol in nanoemulsions suffers from several disadvantages.

First, the use of ethanol as co-surfactant leads to larger nanoparticles than the use of alcohols with larger carbon chains. Larger particles cause a decrease of the contact surface between skin and nanoemulsion leading to a decrease in the penetration rate. Second, ethanol has a relatively low viscosity of 1.10 cp which is not optimal for the stability of microemulsions. Further, due to the relatively low hydrophobicity of ethanol, the penetration of the nanoemulsions through the lipophilic physiological membranes of the skin may be impaired. As a result, the stability of the nanoemulsion as well as its bioavailability, i.e. penetration into tissues, is reduced. Further, ethanol is a very expensive alcohol compared to other kinds of alcohol such as isopropylalcohol. In addition, ethanol is liable to a special alcohol tax under certain conditions in several countries.

Therefore, it was an object of the present invention to provide a nanoemulsion which overcomes the disadvantages of those mentioned in the prior art and which, in particular, exhibits optimal physical properties which may improve the stability as well as penetration into cells and tissues, while at the same time being less expensive than the nanoemulsions of the state of the art.

5-Aminolevulinic acid is used as a prodrug in the field of photodynamic therapy. Photodynamic therapy is a promising method for the treatment of different pre-malignant and malignant diseases which are associated with cell proliferation (Taylor EL and Brown SB, 2002, Journal of Dermatological treatment, 13, Suppl. 1, S3-11 and Peng Q. et al., 1997, Cancer, 79, S2282-2308). The principle of photodynamic therapy is based on the introduction of a so-called photosensitizing agent into the lesioned tissue and subsequent radiation with light of appropriate wavelength in order to transform the agent into a cytotoxically active agent which, in turn, causes the destruction of the cell. The selectivity of this method is due to the enhanced concentration of the sensitizing agent in fast-proliferating or lesioned cells in comparison to normal tissue. Furthermore, irradiation of the photosensitizer gives rise to a characteristic fluorescence radiation which can be used for diagnostic purposes, for example, for detecting proliferating cells.

5-Aminolevulinic acid is an endogenous substance which is synthesized from glycine and succinyl-CoA within the cells. Within the scope of heme biosynthesis, the protoporphyrin IX, which is photoactive to a high degree, is formed from 5-aminolevulinic acid (5-ALA) and is then converted into heme. This control mechanism is circumvented by exogenously administering synthetically prepared 5-aminolevulinic acid, thereby giving rise to an increased production of protoporphyrin IX. Since the degradation of protoporphyrin fX is further inhibited by the natural control mechanism, this compound becomes concentrated in the cells. When irradiated with light, protoporphyrin IX is able to undergo a photochemical oxidation reaction and consequently acts as a photosensitizer for the photodynamic therapy.

Systemic applications of 5-aminolevulinic acid are associated with a number of side effects which can be circumvented with topical application of the drug. A number of investigations using topically applicable 5-aminolevulinic acid compositions are known from the prior art. While these investigations have the feature in common that the 5-aminolevulinic acid employed is in the form of an oil-in-water emulsion, differences exist with regard to other parameters such as period of penetration, period of treatment, type of light employed and the dose of light employed.

Thiele et al. (H+G, Vol. 69, No. 3, pp 161-164 (1994)) describe investigations which involve using 20% 5-aminolevulinic acid in the form of an oil-in-water emulsion, with a penetration period of from 5 to 6 h, and subsequently irradiating with an argon ion-pumped dye laser (emission peak 630 nm) giving a cumulative total dose of from 50 to 100 $J/cm^2$.

Wolf et al. (Journal of the American Academy of Dermatology, Vol. 28, pp. 17-21, 1993) describe investigations which involve using 20% 5-aminolevulinic acid in the form of an oil-in-water emulsion, with a penetration period of 4, 6 or 8 h, and irradiating with unfiltered light or red light, giving a light dose of from 30 $J/cm^2$ to 100 $J/cm^2$.

Although the investigations disclosed in the prior art clearly demonstrate the promising potential of photodynamic therapy using 5-aminolevulinic acid, oil-in-water emulsions known so far suffer from a number of disadvantages.

For example, M. Novo Rodriguez et al. (SPIE, Vol. 2371, pp. 204-209) showed that, in the high concentrations required for a clinical application, aminolevulinic acid is unstable in aqueous solutions in a neutral to basic pH range. During the investigation period of 25 h, satisfactory results are only obtained at a concentration of 3% and at a pH of 5, which are specified as the optimal conditions for aqueous solutions of 5-aminolevulinic acid. For clinical use, however, it will in general be necessary to provide also compositions in a higher concentration range; furthermore, to be used commercially, the 5-ALA solutions have to be stable for a period which is in the dimension of weeks or months.

von Arx et al. (J. Pharm. Pharmacol. 49: 652-656, 1997) describe investigations relating to the topical application of 5-aminolevulinic acid in a variety of gels. This publication states that the best formulation for maintaining the stability of 5-aminolevulinic acid is a combination with Novion AA-1, a polyacrylic acid, at a pH <6.

Harlimann et al. (Dermatology, Vol. 197, No. 3, 1998, pp. 248-254) disclose nanocolloid lotions containing 5-aminolevulinic acid as well as the use thereof in photodynamic therapy, without further specifying the emulsion.

WO 00/28971 describes compositions comprising a nanoemulsion and 5-aminolevulinic acid, wherein the nanoemulsion consists of egg lecithin (83% phosphatidylcholine), Miglyol 812 (triglyceride) and polysorbate 80 in 20 mM phosphate buffer (see Example 1 of WO 00/28971), but no alcohol is used as solvent. Nanocolloid formulations containing egg lecithin as an emulsifier, however, suffer from the disadvantage that they are markedly stronger colored than 5-aminolevulinic acid nanoemulsions containing soy lecithin as an emulsifier. The color change in the formulation correlates with the formation of a degradation product of the active agent 5-aminolevulinic acid. It is to be concluded therefrom that nanoemulsion formulations containing egg lecithin involve considerably reduced stabilization of 5-aminolevulinic acid compared to formulations containing soy lecithin as an emulsifier.

Another disadvantage of the known oil-in-water emulsions in combination with 5-aminolevulinic acid is that the penetration depth of the photosensitizer into the damaged tissue is not optimal. As a result, the diseased tissue is amenable to photodynamic therapy only in its superior layers although the penetration depth of the light used for activating the photosensitizer would also allow treatment of more deeply lying layers.

Therefore, it was a further object of the present invention to provide compositions comprising 5-aminolevulinic acid, which, at least partially, overcome the known disadvantages of the state of the art.

SUMMARY OF THE INVENTION

This object is achieved according to the present invention by providing a nanoemulsion comprising a) at least one aqueous component and b) a carrier, which comprises i) at least one lipophilic component, ii) at least one surfactant and iii) at least one alcohol, wherein the at least one alcohol has at least three carbon atoms.

The present invention relates to a nanoemulsion comprising at least one aqueous component and a carrier, wherein the carrier comprises at least one lipophilic component, at least one surfactant and at least one alcohol. The present invention further relates to a composition comprising said nanoemulsion and an active agent. In particular, the composition is present as a gel and the active agent is 5-aminolevulinic acid (ALA), a derivative, precursor and/or metabolite thereof. The invention further relates to the preparation of said nanoemulsion and/or composition and to their use for the treatment of dermatological diseases, virus-associated diseases as well as diseases associated with cell proliferation, in particular, tumor diseases and/or psoriasis. The present invention is further directed to the use of said nanoemulsion in cosmetics.

BRIEF DESCRIPTION OF THE DRAWINGS

The Figures and the following Examples are intended to further illustrate the invention.

DETAILED DESCRIPTION OF THE INVENTION

The inventors have now discovered that a nanoemulsion according to the invention has an optimally lower mean particle size with a narrow particle-size distribution.

The amount of component i) of the carrier, i.e. the lipophilic component, is preferably present in an amount of from 0.1% by weight to 15% by weight, more preferably from 1% by weight to 8% by weight and most preferably from 3% by weight to 4% by weight, based on the total weight of the nanoemulsion. The amount of component ii) of the carrier, i.e. the surfactant or surfactants, is preferably present in an amount of from 1% by weight to 30% by weight, more preferably from 2% by weight to 15% by weight and most preferably from 4% by weight to 6% by weight, based on the total weight of the nanoemulsion. The amount of component iii) of the carrier, i.e. the alcohol, is preferably present in an amount of from 0.1% by weight to 10% by weight, more preferably from 0.5% by weight to 5% by weight and most preferably from 1% by weight to 2% by weight, based on the total weight of the nanoemulsion.

The aqueous component is preferably present in the nanoemulsion in an amount of from 50% by weight to 98% by weight, more preferably from 70% by weight to 95% by weight and most preferably from 88% by weight to 92% by weight, based on the total weight of the nanoemulsion. Advantageously, this specific constitution of the nanoemulsion leads to a nanoemulsion which is highly tolerable to the skin and does not result in a sticky feel during application to the skin, which, inter alia, is due to the relatively low proportion of surfactants and lipophilic components.

In a preferred embodiment of the present invention, the nanoemulsion comprises as surfactant a membrane-forming surfactant and an O/W-emulsion-forming co-surfactant. The weight ratio of the amount of membrane-forming surfactant: O/W-emulsion-forming co-surfactant ranges from 0.1:1 to 10:1, preferably from 0.2:1 to 0.8:1, more preferably from 0.4:1 to 0.6:1.

A preferred alcohol having at least 3 carbon atoms within the scope of the present invention is an alcohol having 3-10 carbon atoms, preferably 3-7 carbon atoms, more preferably 3-5 carbon atoms, and most preferably 3 carbon atoms. Particularly suitable alcohols having 5 carbon atoms are 1-pentanol and/or 4-methyl-2-pentanol. Suitable alcohols having 4 carbon atoms are 1-butylalcohol, tert-butylalcohol (2-methyl-2-propanol) and/or sec-butylalcohol (2-butanol). Most preferred are alcohols having 3 carbon atoms, namely 1-propylalcohol and isopropylalcohol, wherein isopropylalcohol is preferred. By using a $C_3$-alcohol, in particular, isopropylalcohol in the inventive nanoemulsion, the present inventors have discovered that the nanoemulsion shows a reduced particle size and narrower particle-size distribution as well as improved stability and an enhanced penetration into tissues compared to the nanoemulsions of the state of the art using ethanol as alcohol. This was surprising, as isopropanol and ethanol are very similar in their physiological and chemical features.

When isopropanol is used as alcohol in the inventive nanoemulsion, the size of the emulsified particles is smaller compared to the use of ethanol. Due to the resulting increased contact surface of the nanoemulsion with the skin, the penetration properties are increased. The reduction of the particle size is also decisive for an improved stability of the nanoemulsion since it is known that the rate of particle agglutination ultimately leading to phase separation increases with the particle size. The advantageous effects of isopropanol may be due to its slightly higher hydrophobicity, which may result in a better ability to penetrate through the lipophilic physiological membranes. Further, isopropanol has a higher viscosity (cp at 25° C. of 2.32) compared to ethanol (viscosity/cp, 25° C., 1.10). Said higher viscosity of isopropanol may serve for a better stabilization mechanism in nanoemulsions, as viscosity reduces the mobility of molecules. A further advantage of isopropanol compared to ethanol is that it is available at relatively low cost's, which is about ⅓ of the costs of ethanol, and free of an additional alcohol tax.

Preferably, the at least one lipophilic component of the carrier of the inventive nanoemulsion is a lipid, a vegetable oil and/or an animal oil. Suitable lipids according to the present invention are physiologically acceptable lipids such as ceramide, mono-, di- and triacylglycerin (triglycerides), in particular, caprylic and/or capric triglyceride and/or a mixture thereof, particularly preferably Miglyol (such as Miglyol 812 or Myritol 318 available e.g. from Henkel). Suitable vegetable and animal oils e.g. are sunflower oil, soybean oil, peanut oil, rape oil, fish oil and/or cetaceum.

A suitable membrane-forming surfactant is a phospholipid, a lysophospholipid, a ceramide and/or a mixture thereof. Preferably, the phospholipid is lecithin or cephalin from soybeans or hens' eggs, more preferably the lecithin is soy lecithin.

Preferably, the lecithin has a phosphatidylcholine content of at least 80% by weight, more preferably of at least 90% by weight, and most preferably of at least 94% by weight. The inventors have found that the quality of the lecithin, namely its phosphatidylcholine content, plays a crucial role for the size of the particles of the nanoemulsion. The higher the phosphatidylcholine content of the lecithin, the smaller is the size of the particles of the nanoemulsion.

As O/W emulsion-forming co-surfactant, anionic, nonionic, cationic and/or amphoteric surfactants are suitable as well as block copolymers. Suitable anionic surfactants are soaps, alkylbenzene sulphonates, alkane sulphonates, alkylsulfates and/or alkyl ether sulfates. Suitable cationic surfactants are quaternary ammonium compounds, preferably having one or two hydrophobic groups (e.g. cetyltrimethylammonium bromide and cetyltrimethylammonium chloride) and/or salts of long-chain primary amines. A suitable amphoteric surfactant is N-(acylamidoalkyl)betaine, N-alkyl-ca-aminopropionate and/or amine-N-oxide. A suitable block compolymer, for example, is propylene oxide. In the scope of the present invention, a nonionic surfactant is particularly preferred as O/W emulsion-forming co-surfactant. A suitable nonionic surfactant is selected from the group consisting of fatty alcohol polyglycolether, alkylphenol polyglycolether, alkylpolyglucoside, fatty acid glucamide, fatty acid polyglycolether, ethylen oxide-propylene oxide-block polymer, polyglycerol fatty acid ester, fatty acid alcanolamide and (ethoxylated) sorbitane fatty acid ester (sorbitane). A particularly preferred ethoxylated sorbitane fatty acid ester is polyoxyethylene sorbitane monooleate, most preferably Polysorbate 80.

The aqueous component of the nanoemulsion of the present invention preferably comprises a weak buffer system with low salt content, more preferably a 5 mM to 30 mM phosphate buffer and most preferably 10 mM phosphate buffer. The pH value of the phosphate buffer preferably ranges from pH 4 to pH 8, more preferably from pH 5 to pH 7, and is most preferably from pH 5.5 to pH 6.5. The water used for preparing the phosphate buffer is preferably sterile deionized water and/or water for injections, more preferably water for injections.

The mean diameter of the emulsified particles in the nanoemulsion (nanosomes) is 5 nm to 500 nm, preferably 10 nm to 200 nm, more preferably less than 100 nm, particular, up to 90 nm, preferably up to 70 nm, still more preferably 10 nm to 50 nm, and most preferably 15 nm to 35 nm. The size distribution of the nanoparticles is preferably monodisperse and follows Gaussian distribution. The diameter of the emulsified particles of the invention is determined by means of the particle size distribution, which is measured by the method of dynamic light scattering (DLS) (also called photon correlation spectroscopy (PCS)). The statistical analysis of the distribution of the particles is performed by a method called particle number-weighted distribution in accordance with the present invention.

A further subject of the present invention is a process for the preparation of the nanoemulsion according to the invention, comprising the following steps: a) providing an aqueous component, b) providing a carrier comprising at least one lipophilic component, at least one surfactant and at least one alcohol, wherein the at least one alcohol has at least three carbon atoms, and c) mixing the aqueous component of step a) with the carrier of step b). By preparing the nanoemulsion, the components of the carrier are provided in the aqueous component and the mixture is converted into a nanoemulsion by intensive or gentle homogenization. Homogenization may be carried out, for example, by commercially available homogenizers. After the preparation of the nanoemulsion, further additives and excipients may be added, the presence of which is not appropriate during the homogenization.

The process for the preparation of a nanoemulsion preferably is performed under aseptic conditions, e.g. using a laminar flow hood.

The inventors found out that, besides the composition, some steps of the process of preparation are decisive for the final size and particle-size distribution of the emulsified particles in the nanoemulsion. Particularly, temperature and homogenisation conditions during step c play a major role. Step c is carried out at a temperature between 50 to 60° C. All ingredients are previously heated up to this temperature. The container and the mixer should also be optimized to achieve a very fast homogenous mixture of the components (within seconds) avoiding formation of foam. See Example 1 for an illustration of such procedure. Alternatively, the homogenization does not require high shear devices such as sonicators or high-pressure homogenizers.

A further aspect of the present invention is a pharmaceutical and/or cosmetic composition comprising the inventive nanoemulsion. The inventive nanoemulsion is suitable in the field of cosmetics, e.g. as anti-aging agent, as it provides an elegant, translucent and transparent vehicle that can be used for a variety of different product types. The nanoemulsion provides a system in very delicate balance, which has relatively low levels of emulsifiers that are considered as irritating. The inventive nanoemulsion retains the desirable transparency or translucency, it is able to accommodate a reasonable amount of additives such as fragrances or moisturizers, while remaining stable, mild and gentle on the skin of the user due to the low level of emulsifier. For the intended use of the final product in the case of cosmetics, it is possible to add non-therapeutic or non-active agents such as emollients, flavors, colorants, fragrances, gellants, thickeners, sunscreens and the like, which enhance the ultimate use of a product, particularly for topical cosmetic purposes, and provided care is taken to avoid choosing components that will interfere with the clarity of the product. The final product can take the form of a milk, cream, lotion, gel, serum or liquid spray, among others. In the case of sunscreens the nanoemulsions of the invention may incorporate one or more sunscreen agents such as benzophenones, avobenzones, cinnamates, salicylates and the like.

The nanoemulsions may also be employed in pharmaceutical compositions, in particular, they can be used for the manufacture of a topical medicament for the treatment of dermatological diseases such as neurodermatitis, psoriasis, keratosis, in particular, actinic keratosis, and diseases associated with cell proliferation such as tumor diseases. Preferably, the tumor disease is selected from the group consisting of basal cell carcinoma, squamous cell carcinoma, Morbus Bowen, vulvar intraepithelial neoplasia (VIN) or a nodular or subcutaneous cancer disease. Further, the nanoemulsion is suitable for the treatment of virus-associated diseases caused by a human papilloma virus such as *Condylomata acuminata*. By incorporating the lipophilic component of the nanoemulsion, the transepidermal loss of water can be influenced advantageously, i.e. the barrier function of the skin can be enhanced and, thus, dermatological diseases such as neurodennatitis can be affected advantageously.

A further aspect of the present invention relates to a composition comprising the inventive nanoemulsion and an active agent. In this respect, the composition is particularly useful as a pharmaceutical and/or cosmetic composition, e.g. for application to the skin or hair. The nanoemulsions of the invention comprised in said compositions provide a very efficient delivery system for a wide variety of active agents. Examples of active agents that may be useful include agents for the eradication of age spots, keratoses and wrinkles, analgesics, anesthetics, anti-acne agents, antibacterials, antiyeast agents, antifungal agents, antiviral agents, anti-dandruff agents, antidermatitis agents, antipruritic agents, antiemetics, antimotion sickness agents, anti-inflammatory agents, anti-hyperkeratolytic agents, anti-dry skin agents, antiperspirants, antipsoriatic agents, antiseborrheic agents, hair conditioners and hair treatment agents, anti-aging agents, antiwrinkle agents, antiasthmatic agents and bronchodilators, sunscreen agents, anti-histamine agents, skin lightening agents, depigmenting agents, vitamins, corticosteroids, hormones, retinoids such as retinoic acid and retinol, topical cardiovascular agents, clotrimazole, ketokonazole, miconazole, griseofulvin, hydroxyzine, diphenhydramine, pramoxine, lidocaine, procaine, mepivacaine, monobenzone, erythromycin, tetracycline, clindamycin, kanamycin, meclocyline, hydroquinone, minocycline, naproxen, ibuprofen, theophylin, cromolyn, albuterol, topical steroids such as hydrocortisone, hydrocortisone 21-acetate, hydrocortisone 17-valerate, and hydrocortisone 17-butyrate, betamethasone valerate, betamethasone diproprionate, triamcinolone acetonide, fluocinonide, clobetasol proprionate, benzoyl peroxide, crotamiton, propranolol, promethazine, vitamin A palmitate, vitamin E acetate and mixtures thereof.

In a preferred embodiment of the present invention the active agent is selected from the group consisting of 5-aminolevulinic acid, a derivative, precursor and/or metabolite thereof. "Derivative" is to be understood as being, in particular, an estherification of the amino group of 5-aminolevulinic acid substituted with one or two alkyl groups, particularly preferably with one methyl group. The most preferred derivate is methylaminolevulinic acid. The derivatization may be understood also as salt complexes and addition compounds as well as alkylated compounds. "Precursor" and "metabolite" are to be understood as substances converted in a cell into protoporphyrin IX. The active agent 5-aminolevulinic acid or a derivative thereof is especially preferred.

According to the present invention this object is achieved by providing a composition comprising the inventive nanoemulsion and 5-aminolevulinic acid, a derivative, precursor and/or metabolite thereof as active agent. In these compositions, the above-mentioned advantageous properties with respect to stability, penetration into tissues as well as lower costs of the inventive nanoemulsions can be utilized to transport a 5-aminolevulinic acid to target sites of tissues.

A specific interaction has been found between aminolevulinic acid and the nanoparticles of the emulsion. In particular, 5-aminolevulinic acid, a derivative, precursor and/or metabolite thereof, is attached at the outside of the monolayer of the nanoparticles of the nanoemulsion. Thus, aminolevulinic acid is transported by the particles while it is not contained within the core of the particles. Rather, aminolevulinic acid is located outside the core of the particles due to interactions between aminolevulinic acid and the outer monolayer. In conventional nanoemulsions, in contrast thereto, the drug is contained inside the lipid core of the particles of nanoemulsions.

Surprisingly, it has been found that the stability of 5-aminolevulinic acid can be considerably increased when the 5-aminolevulinic acid is formulated with the inventive nanoemulsion comprising at least one alcohol which has at least three carbon atoms. While the reasons for this are not known, it appears that a microenvironment created by nanosomes has a particularly favorable effect on the stability of 5-aminolevulinic acid.

It also turned out, surprisingly, that an improved cell and tissue penetration can be achieved with the nanoemulsions according to the invention, resulting in more deeply lying diseases and/or diseases with higher layer thicknesses also becoming accessible to treatment. The greater penetration depths were surprising especially because it had previously been assumed that, due to its small size, 5-aminolevulinic acid would in any case be readily able to penetrate through a damaged epidermis which is present, for example, in tissue associated with inflammations, precancerous stages and tumors.

A third surprising advantage is that, when formulated with nanosomes according to the invention, 5-aminolevulinic acid is evidently taken up very efficiently from the cells. This firstly improves targeting; secondly, it means that the penetration period, i.e. the time between applying the composition and irradiating the diseased tissue with light, can be reduced, which means a distinct relief for the patient. As can be gathered from Example 4, FIG. 5, 5-aminolevulinic acid uptake into cultured cells and conversion of aminolevulinic acid to PpIX within the cells is enhanced with increasing concentrations of the inventive nanoemulsion with constant concentration of aminolevulinic aci.

Storage stability, too, can be improved by means of the nanoemulsions of the invention which comprise an alcohol having at least 3 carbon atoms as a solvent in the carrier.

According to the invention the composition preferably comprises an active agent which is selected from 5-aminolevulinic acid, or a derivative, a precursor and/or a metabolite thereof. "Derivative" is to be understood as being, in particular, an estherification of the amino group of 5-aminolevulinic acid substituted with one or two alkyl groups, particularly preferably with one methyl group. Most preferred is 5-aminolevulinic acid or 5-methylaminolevulinic acid. The derivatization may be understood also as salt complexes and additional compounds as well as alkylated compounds. "Precursor" and "metabolite" are to be understood as substances converted in a cell into protoporphyrin IX. The active agent 5-aminolevulinic acid or a derivative thereof is especially preferred.

The size of the emulsified particles in the nanoemulsion (nanosomes) is as given above. The particle size which is in each case optimal depends on further parameters such as the viscosity of the composition. For example, good results were obtained with a nanoemulsion having a viscosity of 1 to 10 mPas at an average particle diameter of less than 100 nm.

The amount of active agent, preferably 5-aminolevulinic acid, in the composition essentially depends on the intended application. In a preferred embodiment, about 1 to 30 wt. % of the active agent, based on the total weight of the composition, are present. Higher or lower doses, however, are also suitable. An amount of preferably 3 to 15 wt. %, has proven to be suitable for applications in connection with photodynamic therapy.

The inventive composition preferably may further comprise at least one preservative and at least one solvent.

In a particularly preferred embodiment, the composition is formulated as a gel. Gel forming agents contained are matrix forming-agents, preferably xanthan. While the particle size of the nanoemulsion in the form of a gel is also preferably less than 100 nm, the viscosity is considerably higher, e.g. 500 to 2000 mPas.

A further aspect of the present invention is a pharmaceutical, cosmetic and/or diagnostic composition which comprises the inventive composition. In this case, the composition can additionally comprise cosmetically and/or pharmaceutically acceptable additives and/or excipients, in particular, substances commonly used in cosmetics or pharmacy. Examples of such substances are buffers, stabilizers, additional emulsifiers, thickeners, etc. Further, the composition is free of constituents which are not pharmaceutically or diagnostically acceptable and preferably free of constituents which, for example, provoke irritation and/or falsify diagnosis. In addition to the carrier substances which have already been mentioned, the pharmaceutical and/or diagnostic preparation can contain further adjuvants or/and additives which are acceptable and preferably well tolerated.

Preferably, the composition is present as liquid, or semi-solid. Suitable liquids within the scope of the present invention are selected from the group consisting of a solution, preferably drops, a spray, an aerosol, an emulsion, or a lotion. Suitable semi-solids within the scope of the present invention are selected from the group consisting of an ointment, a cream (O/W emulsion), a fatty cream (W/O emulsion), a gel, a lotion, a foam, a paste, and/or a suspension.

For dermatological and gynecological applications, the preparation is preferably in a form which is suitable for topical administration, especially in gel form. The preparation possesses properties, e.g. viscosity and rheology, which are favorable for the respective form of application desired to ensure that, after the preparation has been administered, the nanosomes loaded with 5-aminolevulinic acid penetrate to an adequate extent into the target tissue. Said viscosity and rheology properties can be adjusted by adding thickeners such as polyethylene glycol stearyl ethers, polyethylene glycol stearates and/or polysaccharides such as polysaccharide B-1459, for example.

In a particularly preferred embodiment, the inventive composition is a gel. Gels exhibit improved galenic properties compared with the above-mentioned formulations. The inventive gel formulation shows better adhesiveness, stability, release of active agent and tolerance on the skin, and on mucous membranes. The inventive gel preferably comprises 0.01% by weight to 50% by weight, more preferably 0.5% by weight to 30% by weight and most preferably 1% by weight to 20% by weight of the active agent, 1% by weight to 60% by weight, more preferably 15% by weight to 50% by weight, most preferably 10% by weight to 30% by weight of the nanoemulsion, 0.01% by weight to 4% by weight, more preferably 1% by weight to 3% by weight of the at least one filling agent, 1% by weight to 3% by weight of at least one preservative, based on the total weight of the composition, and the balance being the at least one solvent.

A further aspect of the present invention is a process for the preparation of the inventive composition, comprising the following steps:

a) providing an aqueous component,
b) providing a carrier comprising at least one lipophilic component, a least one surfactant and at least one alcohol, wherein the at least one alcohol has at least three carbon atoms,
c) mixing the aqueous component of step a) with the carrier of step b), in order to form a nanoemulsion,
d) adding the active agent prior to and/or after the formation of said nanoemulsion of step c), and
e) optionally adding further additives and/or excipients to step d).

Particularly preferably, the active agent in step d) is added after the formation of said nanoemulsion of step c).

The process is preferably performed under aseptic conditions, e.g. by using a laminar flow hood. The aqueous component, the carrier and the active agent which are employed in the above-mentioned process have the same preferred and suitable meanings as mentioned above. The mixing of the aqueous component with the carrier is preferably performed by intensive homogenization. The 5-aminolevulinic acid and optionally present additives and/or excipients may be added prior to and/or after the homogenization, preferably after the homogenization.

Preferably, air is excluded while carrying out the process, for example, by means of applying a vacuum and/or a protective gas atmosphere. In addition, it is preferred to implement the process while excluding light.

The process is carried out at a temperature at which the desired nanoemulsion can be formed as mentioned above and, for the later steps, the constituents, in particular, the active substance, is adequately stable. In general, it has been found that a temperature range of from about 5 to 30° C. is suitable. However, processing of additives and/or excipients which, for example, are mixed first and homogenized where appropriate, in a separate mixture, and only after that added to the composition, also can be carried out at higher temperatures, for example, up to about 70° C. Especially for pharmaceutical application, care is taken to ensure that the resulting product is sterile, e.g. by using sterile starting materials and by maintaining sterile process conditions or/and by means of a sterilization step following preparation.

In the field of cosmetics, the inventive composition is preferably used as anti-ageing agent, e.g. for eradication of age spots, wrinkles and/or against dry skin.

An important area of use for the compositions according to the invention is in the field of photodynamic therapy, with particular preference being given to applying the nanoemulsion topically. The nanoemulsion according to the invention can be employed in the case of all diseases whose control comprises inhibiting the proliferation of, or destroying, cells or tissues by photoactivating a sensitizer which is formed from 5-aminolevulinic acid. The diseases, in particular, include virus-associated diseases, with the virus preferably being selected from the group of human papilloma viruses (HPV). Most preferably, the virus-associated disease is *Condylomata acuminata*. *Condylomata acuminata* is defined as benign epitheliomas of viral genesis which are almost exclusively localized genitoanally, the pathogen of which is human papilloma virus (HPV) type 6, 11 and 42. In the course of the disease, papules in the size of a pinhead develop cauliflower- and cock's comb-like papillary proliferations.

The compositions of the invention are also suitable for treating dermatological diseases such as diseases associated with keratosis, with actinic keratosis being especially preferred. Actinic keratosis is a squamous cell carcinoma of epidermis in situ. Actinic keratosis is a proliferation of transformed keratinocytes which is limited to epidermis. Actinic keratosis is induced predominantly by chronic exposure to ultraviolet radiation, especially sunlight (also called solar keratosis). Actinic keratosis manifests itself as rough scaling maculae, papules or plaques of from about 1 mm to about 2 cm in diameter.

Further, the inventive compositions are preferably intended for the treatment of diseases associated with increased cell proliferation, since, in that case, the photosensitizer is concentrated to a particularly high degree by the increased cell metabolism in diseased cells.

The compositions according to the invention are consequently suitable for treating tumor diseases such as basal cell adenoma, squamous cell carcinoma, Morbus Bowen, vulvar intraepithelial neoplasia (VIN), and/or nodular and/or subcutaneous cancer diseases. Psoriasis is an example of a non-tumorous disease associated with increased cell proliferation.

The compositions of the invention are especially preferred for the treatment of basal cell adenoma. Basal cell adenoma is characterized as an epithelial tumor which grows local-invasively and destructively, however, metastasizes only very seldom and, therefore, is considered as semi-malignant. It is mainly located (80%) in the head and neck region, especially in the region of the forehead, canthus and nose. In the case of unfavorable progression, tissue destruction and even death result, e.g. by bone and vascular erosion and bleeding associated therewith, as well as by CNS invasion. Basal cell adenoma originates from degenerative cells of the germ layer (basal cell layer) of the epidermis and/or the outer root sheath of the hair follicles. In contrast to healthy basal cells which normally lose their division capacity when passing through the epidermis, decay and reform the corneum, basalioma cells maintain their division capacity and are no longer capable of forming a horny layer.

The invention further relates to the use of the nanoemulsion according to the invention for the manufacture of a medicament in photodynamic therapy.

Thus, treatment of the above-mentioned diseases is effected, for example, by topically applying a nanoemulsion which contains the active agent, e.g. 5-aminolevulinic acid, and subsequently incubating in order to allow an adequate quantity of the 5-aminolevulinic acid to penetrate into the tissue which is being treated. During the incubation, irradiation of the treated area with light is preferably avoided, for example, by covering it, in order to prevent any undesirable premature activation. After the incubation period, which is generally from about 1 to 8 h and usually about 4 h, has expired, the tissue is irradiated with an adequate dose of radiation using a light source. Suitable light sources include lamps emitting white light and also monochromatic light sources. The radiation doses are normally in a range of from about 20 $J/cm^2$ to several 100 $J/cm^2$ per application.

Another field of applying the 5-aminolevulinic acid gel according to the invention relates to the detection of the presence of proliferating cells in a sample, for example in a tissue sample. Detection is based on selectively concentrating a photosensitizer, which is produced by metabolism of the active agent, in proliferating cells as compared with normal cells. Preferably, the active agent is 5-aminolevulinic acid and the photosensitizer is protoporphyrin IX. The extent to which the photosensitizer has been concentrated can be determined by means of photodiagnostic methods, for example, by irradiating with light having a wavelength of 405 nm and measuring the fluorescence radiation generated by the photosensitizer. The nanoemulsions according to the invention are particularly suitable for use in tumor diagnosis.

Further, the invention relates to a kit which comprises a composition according to the invention comprising the inventive nanoemulsion and 5-aminolevulinic acid, a derivative, precursor and/or metabolite thereof which is suitable for being applied topically, and one or more auxiliary substances. Examples of these auxiliary substances are an essential photoresist covering material such as a plastic film which is applied to the site to be treated after the nanoemulsion has been applied to said site in order to prevent premature activation by light, and means for attaching the covering material or else means for applying the nanoemulsion to the site to be treated.

Further, the invention relates to a method of treating a virus-associated disease, a dermatological disease and/or a disease associated with cell proliferation comprising administering a pharmaceutically effective amount of the inventive composition to a subject in need thereof. Preferably, the subject is a mammal, more preferably a human.

A further aspect of the present invention relates to a composition comprising an active agent selected from the group consisting of 5-aminolevulinic acid, a derivative, precursor and/or metabolite thereof, and a nanoemulsion, wherein the nanoemulsion comprises an alcohol. Preferably, the composition and, in particular, the nanoemulsion further comprise at least one aqueous component, preferably water, and at least one lipophilic component and/or at least one surfactant.

5-aminolevulinic acid, a derivative, precursor and/or metabolite thereof which is suitable for being applied topically is used. "Derivative" is to be understood as being, in particular, an estherification of the amino group of 5-aminolevulinic acid substituted with one or two alkyl groups, particularly preferably with one methyl group. Most preferred is 5-aminolevulinic acid or 5-methylaminolevulinic acid. The derivatization may be understood also as salts complexes and addition compounds as well as alkylated compounds. "Precursor" and "metabolite" are to be understood as substances converted in a cell into protoporphyrin IX. The active agent 5-aminolevulinic acid or a derivative thereof is especially preferred.

As alcohol, a $C_2$ to $C_8$ alcohol, in particular, a $C_3$ to $C_8$ alcohol, is preferred, and isopropanol and/or I-propyl alcohol is still more preferred for the reasons given above.

Preferably, the aminolevulinic acid, a derivative, precursor and/or metabolite thereof is attached at the outer monolayer of the particles of the nanoemulsion. The aminolevulinic acid is thus located outside the core of the particles which is due to interactions between aminolevulinic acid and the outer monolayer.

Preferably, the at least one lipophilic component is Miglyol, the at least one surfactant is lecithin, preferably soy lecithin and/or a polyoxyethylene-type surfactant, preferably Polysorbate 80.

A further aspect of the invention relates to a pharmaceutical and/or diagnostic composition comprising the above-mentioned composition.

A further aspect of the present invention relates to the use of said nanoemulsion in pharmaceutical compositions, in particular, for the manufacture of a medicament for the treatment of dermatological diseases such as psoriasis, keratosis and, in particular, actinic keratosis. Further, the composition is suitable for diseases associated with cell proliferation such as tumor diseases, e.g. basal cell carcinoma, squamous cell carcinoma, Morbus Bowen, vulvar intraepithelial neoplasia (VIN) or nodular and/or subcutaneous cancer disease. Further, the composition is suitable for the treatment of virus-associated diseases such as *Condylomata acuminata*.

Another aspect of the invention relates to a composition comprising a nanoemulsion and an active agent, wherein the active agent is attached at the outer monolayer of the particles of the nanoemulsion. This is particularly useful for enhancing the chemical properties (e.g. stability) and pharmaceutical properties (e.g. penetration depth into skin and bioavailability) of the active agent.

Preferably, the nanoemulsion and/or the active agent is defined as for the composition described above (see page 9 of the description).

A further aspect relates to a pharmaceutical and/or cosmetic composition comprising the composition, wherein the active agent is attached at the outer monolayer of the particles of the nanoemulsion.

Encompassed by the present invention is also the use of a composition comprising a nanoemulsion and an active agent, wherein the active agent is attached at the outer monolayer of the particles of the nanoemulsion for the manufacture of a medicament for the treatment of a virus-associated, dermatological, cell-proliferation-associated disease and/or in the photodynamic therapy. Preferred embodiments of said diseases and the photodynamic therapy are as mentioned above.

EXAMPLES

Example 1: Preparation of Nanoemulsion BF200

TABLE 1

Composition of nanoemulsion BF200

| Ingredient | % (w/w) | Function | Quality |
|---|---|---|---|
| Soy lecithin | 1.73 | Surfactant | >94% Phosphatidylcholine, for pharmaceutical use, USP |
| Polysorbate 80 (polyoxyethylene sorbitol monooleate) | 3.40 | Co-surfactant | Ph. Eur. |
| Caprylic/capric triglycerides | 3.45 | Lipid core | Ph. Eur. |
| Isopropyl alcohol | 1.42 | Solvent | Ph. Eur. |
| 10 mM Phosphate buffer, pH 6 | ad 100.00 | Solvent | Water for injection: Ph. Eur Disodium phosphate and sodium hydrogen phosphate: Ph. Eur. |

The manufacturing process for the emulsion BF200 consists of the following steps:
Step 1: Preparation of a 10 mM phosphate buffer, pH 6 (aqueous component).
Step 2: Preparation of a carrier containing the lipophilic component, the surfactants and the alcohol.
Step 3: Manufacturing of the nanoemulsion by mixing the aqueous component from Step 1 and the carrier from Step 2.
Step 4: Filter sterilisation and filling of the nanoemulsion BF200 into sterile glass bottles under laminar flow hood.

Description of the manufacturing process for a typical batch size:
Step 1: 10 mM phosphate buffer (1000 g), pH 6, was prepared and the phosphate buffer was sterilized by filtration through a 0.2 μm sterile filter.
Step 2: Preparation of a carrier containing the lipophilic component, the surfactants and the alcohol.

TABLE 2

Carrier

| Ingredients | Weight (g) |
|---|---|
| Soy lecithin | 17.30 |
| Polysorbate 80 | 34.00 |
| Caprylic, capric triglyceride | 34.50 |
| Isopropyl alcohol | 14.20 |

Soy lecithin (17.30 g) was weighed in a suitable vessel. Isopropyl alcohol (14.20 g) was added and the vessel was covered to avoid alcohol evaporation. Soy lecithin was dissolved under continuous stirring with a suitable stirrer at room temperature. Caprylic/capric triglycerides (34.50 g) and Polysorbate 80 (34.00 g) were weighed and added to the solution of soy lecithin. The mixture was stirred with a suitable stirrer at room temperature until a homogenous clear solution was obtained. This solution is the concentrate containing all emulsifiers and lipid components of Nanoemulsion BF200.

Step 3: Manufacturing of an emulsion by mixing 900 g phosphate buffer (from Step 1) and 100 g carrier (from Step 2).

First, the aqueous component comprising the phosphate buffer was heated to approximately 55° C. in a suitable vessel. Then, the carrier (concentrate) of step 2 was heated to approximately 55° C. Subsequently, the carrier was poured to the phosphate buffer under continuous stirring with a propeller mixer (700 rpm). The resulting nanoemulsion is stirred for 15 min. The temperature was kept at approximately 55° C. during the whole procedure. Finally, the nanoemulsion was cooled down to room temperature in a water bath.

Step 4: The nanoemulsion was sterilized by filtration through 0.2 µm sterile filter and filled into 100 ml sterile glass bottles under laminar flow hood.

Example 2

Preparation of Aminolevulinic Acid 1%, 3% and 10% and Placebo Gels

The qualitative and quantitative composition of the placebo gel and 1%, 3%, 10% aminolevulinic acid gels are given in the table below.

TABLE 3

Composition of placebo gel

| Ingredient | Amount per gram of gel | Function | Quality |
| --- | --- | --- | --- |
| Xanthan gum | 20.375 mg | Filling agent | Ph. Eur. |
| Nanoemulsion BF200 | 175.0 mg | Carrier | In-house |
| Propylene glycol | 9.0 mg | Preservative | Ph. Eur. |
| Methyl parahydroxy-benzoate | 0.7 mg | Preservative | Ph. Eur. |
| Propyl parahydroxy-benzoate | 0.3 mg | Preservative | Ph. Eur. |
| Water for injection | 794.625 mg | Solvent | Ph. Eur. |

TABLE 4

Composition of aminolevulinic acid 1% gel

| Composition | Amount per gram of gel | Function | Quality |
| --- | --- | --- | --- |
| Aminolevulinic acid hydrochloride | 10.0 mg | Drug substance | In-house |
| Xanthan gum | 20.125 mg | Filling agent | Ph. Eur. |
| Nanoemulsion BF200 | 175.0 mg | Carrier | In-house |
| Propylene glycol | 9.0 mg | Preservative | Ph. Eur. |
| Methyl parahydroxy-benzoate | 0.7 mg | Preservative | Ph. Eur. |
| Propyl parahydroxy-benzoate | 0.3 mg | Preservative | Ph. Eur. |
| Water for injection | 784.875 mg | Solvent | Ph. Eur. |

TABLE 5

Composition of aminolevulinic acid 3% gel

| Ingredient | Amount per gram of gel | Function | Quality |
| --- | --- | --- | --- |
| Aminolevulinic acid hydrochloride | 30.0 mg | Drug substance | In-house |
| Xanthan gum | 19.625 mg | Filling agent | Ph. Eur. |
| Nanoemulsion BF200 | 175.0 mg | Carrier | In-house |
| Propylene glycol | 9.0 mg | Preservative | Ph. Eur. |
| Methyl parahydroxy-benzoate | 0.7 mg | Preservative | Ph. Eur. |
| Propyl parahydroxy-benzoate | 0.3 mg | Preservative | Ph. Eur. |
| Water for injection | 765.375 mg | Solvent | Ph. Eur. |

TABLE 6

Composition of aminolevulinic acid 10% gel

| Ingredient | Amount per gram of gel | Function | Quality |
| --- | --- | --- | --- |
| Aminolevulinic acid hydrochloride | 100.0 mg | Drug substance | In-house |
| Xanthan gum | 17.875 mg | Filling agent | Ph. Eur. |
| Nanoemulsion BF200 | 175.0 mg | Carrier | In-house |
| Propylene glycol | 9.0 mg | Preservative | Ph. Eur. |
| Methyl parahydroxy-benzoate | 0.7 mg | Preservative | Ph. Eur. |
| Propyl parahydroxy-benzoate | 0.3 mg | Preservative | Ph. Eur. |
| Water for injection | 697.125 mg | Solvent | Ph. Eur. |

The manufacturing process for placebo or aminolevulinic acid gel consists of the following steps:

Step 1: Manufacturing of the gel base by addition of xanthan gum to water for injection, mixing and steam sterilisation Step 2: Preparation of a concentrated solution of preservatives of methyl parahydroxybenzoate and propyl parahydroxybenzoate in propylene glycol Step 3, for placebo: Preparation of the final gel formulation by addition of the concentrated solution of preservatives to the gel base, addition of Nanoemulsion BF200 to the gel base and homogenising of the gel.

Step 3, for aminolevulinic acid gels: Preparation of the final gel formulation by addition of the concentrated solution of preservatives to the gel base. Preparation of a solution of aminolevulinic acid hydrochloride in Nanoemulsion BF200. Addition of the aminolevulinic acid hydrochloride solution in Nanoemulsion BF200 to the gel base and homogenising of the gel.

Description of the Manufacturing Process:

Step 1: Preparation of Gel Base with Xanthan Gum

A Stephan bowl was disinfected with isopropanol 70%. Water for injection (97.50 unit amount) was put into the bowl and then Xanthan (2.5 unit amount) was spread thereon. The mixture was dispersed in vacuum at a pressure of approximately 100 mbar per minute at 600 revolutions for 90 min. The resulting basis gel was filled in 200 ml Schott flasks which has been rinsed before with water for injection (filled ⅓ at most). The basis gel in the flasks was then steam sterilized in an autoclave for 20 min at 121° C.

Step 2: Preparation of Parabeni Conc.

Methylparahydroxybenzoic acid (7.0 parts) and propylparahydroxybenzoic acid (3.0 parts) were weighed into a suitable vessel. Propylene glycol (90 parts) was admixed thereto and the parahydroxybenzoates were dissolved in propylene glycol. The mixture was heated on a heater plate while stirring with a magnetic stirrer until the mixture dissolved (70° C.) and a clear solution is obtained.

Step 3, Part 1: Preparation of Placebo Gel

TABLE 7

Preparation of placebo gel from base gel and Parabeni conc

|   | Components | Unit Amount |
|---|---|---|
| A | Gel base | 81.50 |
| B | Nanoemulsion BF200 | 17.50 |
| D | Parabeni conc. FH | 1.0 |
|   | Total | 100.0 |

All following steps were carried out in a laminar air flow under aseptic conditions. 1 unit amount parabeni conc. (D) and 81.5 unit amount of basis gel (A) were added to a suitable vessel. 17.5 unit amount of nanoemulsion (B) is filtered through a 0.2 µm sterile filter and added to the base gel. The mixture is stirred for 10 min. Subsequently, 2 unit amount of the gel were each filled into laminated aluminium tubes.

Step 3, Part 2: Preparation of Aminolevulinic Acid 1% Gel

TABLE 8

Preparation of aminolevulinic acid 1% gel

|   | Components | Unit Amount |
|---|---|---|
| A | Basis gel | 80.50 |
| B | Nanoemulsion BF200 | 17.50 |
| C | 5 ALA (aminolevulinic acid hydrochloride) | 1.00 |
| D | Parabeni conc. FH | 1.0 |
|   | Total | 100.0 |

All following operations were carried out in laminar air flow under aseptic conditions. 1 unit amount parabeni conc (D) and 80.5 unit amount of basis gel (A) were given in a suitable vessel. 1 unit amount ALA (C) was dissolved in 17.5 unit amounts of nanoemulsion (B) by gentle stirring until a solution is obtained. Said solution is filterd through a 0.2 µm sterile filter and added to the base gel. The mixture is stirred for 10 min in order to obtain a homogenous gel. Subsequently, 2 g of the gel were each filled into laminated aluminum tubes.

Step 3, Part 3: Preparation of Aminolevulinic Acid 3% and 10% Gel

A 3% and a 10% gel were prepared in the same manner as described for the 1% gel, however, using 78.50 unit amount basis gel and 3 unit amount ALA or 71.50 unit amount basis gel and 10 unit amount ALA, respectively.

Example 3

Particle Size of Nanoemulsion BF-200

Figure 1:
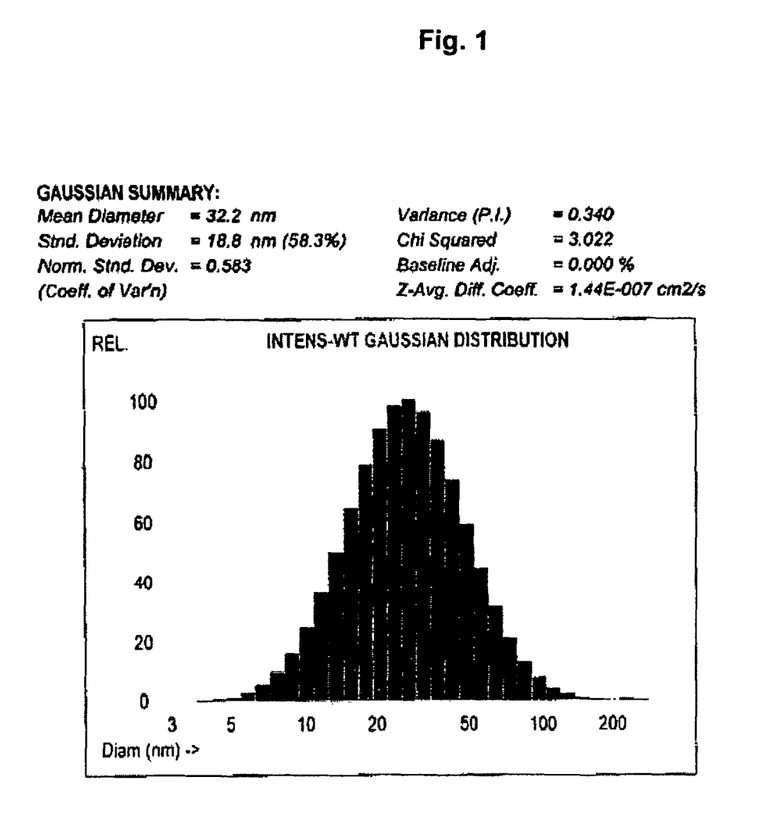
FIG. 1 shows the particle size distribution of a representative batch of Nanoemulsion BF-200 measured by Photon Correlation Spectroscopy.
Figure 2:
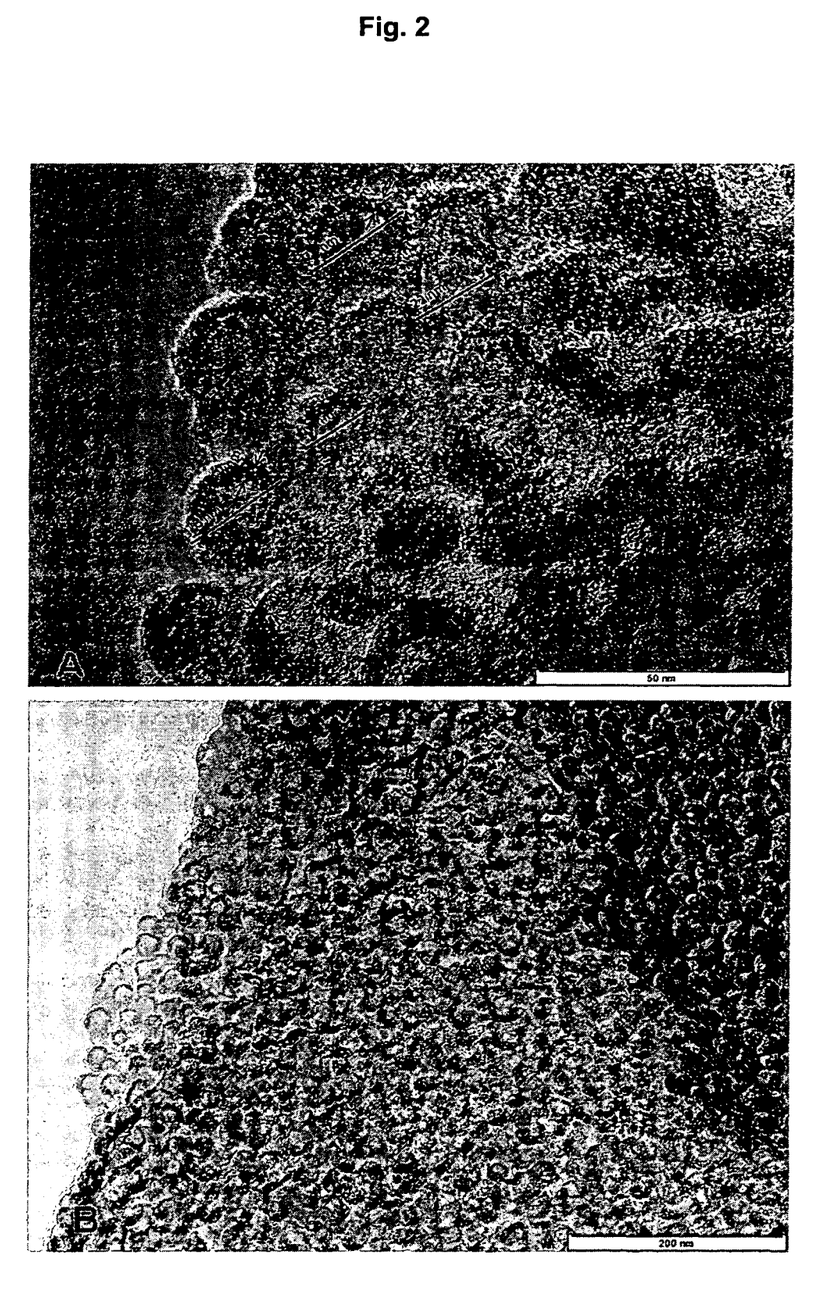
FIG. 2A shows freeze-fracture electron micrographs of Nanoemulsion BF-200 Magnification 1,200,000 times.
FIG. 2B shows Magnification 250,000 times.

The mean particle size of the manufactured nanoemulsion, as assessed by Photon Correlation Spectroscopy, PCS (also called Dynamic Laser Light Scattering, DLS) is less than 100 nm. Furthermore, the nanoemulsion is characterized by a very narrow particle size distribution (see FIG. 1 below).

The nanoemulsion is stable in a wide range of temperatures but can be destroyed by freezing and autoclaving. Nanoemulsions are relatively insensitive to changes in pH and ionic strength and because of their small size they can be sterilized by filtration through a 0.2 µm filter. Nanoemulsions have the potential to improve the delivery of active substances into the skin, thus amplifying the efficacy of topically applied drugs.

Nanoemulsion BF-200 is manufactured using low-energy technology; i.e. the preparation of the nanoemulsion does not require high shear devices, such as sonicators or high-pressure homogenizers.

Investigation of nanoparticles in Nanoemulsion BF-200 was performed by Photon Correlation Spectroscopy and with two electron microscopy techniques: freeze-fracture EM and negative staining.

Photon Correlation Spectroscopy confirmed that BF-200 results in a nanoemulsion with very consistent and reliable particle size and a narrow particle distribution. These characteristics are stable over a long period of time and different temperatures (see Table 9 below).

TABLE 9

Results of a stability study of Nanoemulsion BF-200

| Time point Month | Storage condition Specification | Appearance Slightly opalescent liquid | Viscosity 20° C. pH 5.5-6.5 | Nanoparticle informative mPas | Nanoparticle mean size ≤100 nm | Nanoparticle size distribution 90% ≤ 200 nm | |
|---|---|---|---|---|---|---|---|
| | | | | | | Result | Stnd. deviation |
| 0 | — | >opalescent | 6.2 | n.t. | 15 | 90% < 21 nm | 4.7 |
| 1 | 25° C./60% r.h. | >opalescent | 6.2 | n.t. | 16 | 90% < 22 nm | 4.6 |
| | 40° C./75% r.h. | >opalescent | 6.2 | n.t. | 15 | 90% < 22 nm | 5.7 |
| 2 | 5° C. | >opalescent | 6.2 | 1 | 12 | 90% < 17 nm | 4.2 |
| | 25° C./60% r.h. | >opalescent | 6.2 | 1 | 15 | 90% < 21 nm | 4.7 |
| 3 | 5° C. | >opalescent | 6.2 | 6 | 14 | 90% < 20 nm | 4.7 |
| | 25° C./60% r.h. | >opalescent | 6.1 | 1 | 14 | 90% < 20 nm | 4.8 |

TABLE 9-continued

Results of a stability study of Nanoemulsion BF-200

| Time point | Storage | Appearance Slightly | pH | Viscosity 20° C. | Nanoparticle | Nanoparticle size distribution 90% ≤ 200 nm | |
|---|---|---|---|---|---|---|---|
| Month | condition Specification | opalescent liquid | 5.5-6.5 | informative mPas | mean size ≤100 nm | Result | Stnd. deviation |
| 6 | 5° C. | >opalescent | 6.3 | 6 | 17 | 90% < 23 nm | 5.0 |
|   | 25° C./60% r.h. | >opalescent | 6.3 | 6 | 14 | 90% < 20 nm | 5.2 |
| 12 | 5° C. | >opalescent | 6.2 | 2 | 9 | 90% < 12 nm | — |
|   | 25° C./60% r.h. | >opalescent | 6.1 | 2 | 11 | 90% < 15 nm | — |
| 18 | 5° C. | >opalescent | 6.2 | 10 | 13 | 90% < 18 nm | — |
|   | 25° C./60% r.h. | >opalescent | 6.0 | 8 | 11 | 90% < 15 nm | — |

In summary, all results are within specified limits following up to 12 months of storage at different storage conditions.

Figure 3:
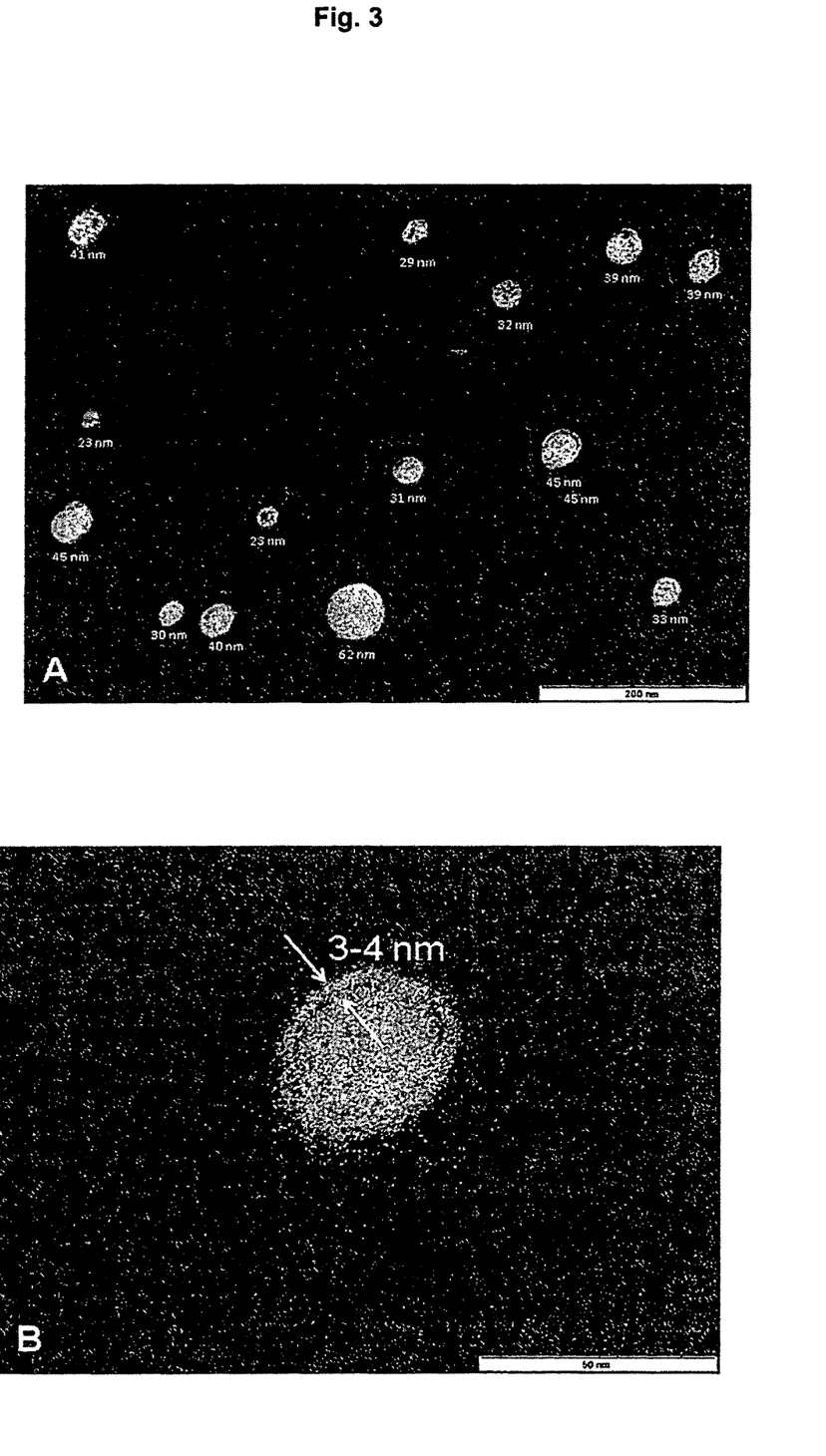
FIG. 3A shows negative staining electron micrographs of Nanoemulsion BF-200 Magnification 1,200,000 times.
FIG. 3B shows Magnification 250,000 times.
Figure 4:
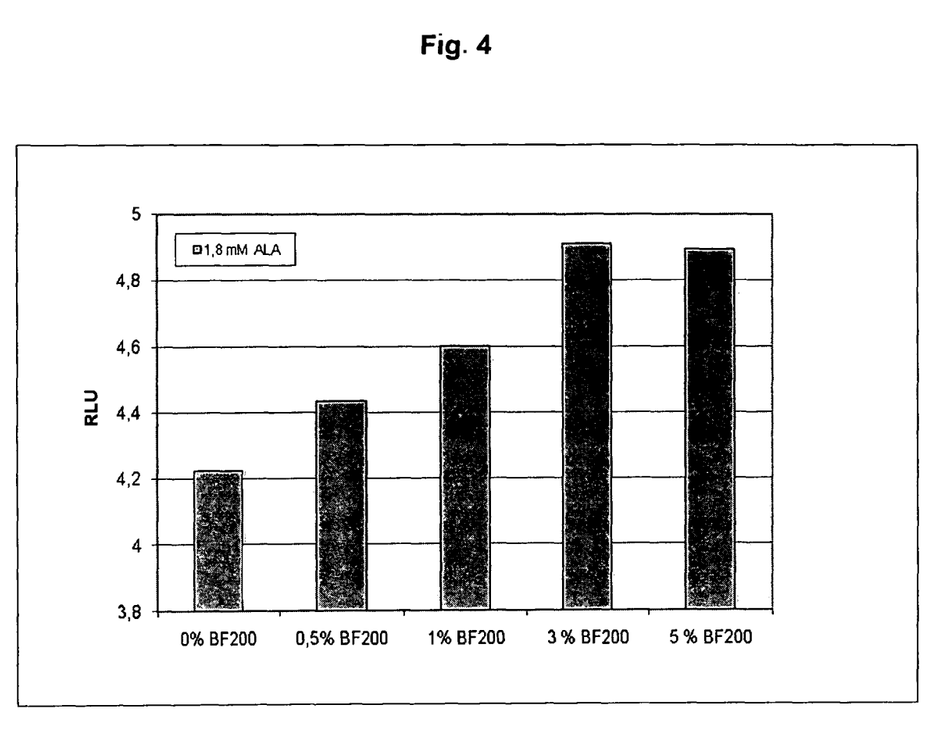
FIG. 4 shows UV-induced PpIX fluorescence measured in Hela cells incubated for three hours with ALA and different concentrations of BF-200. Fluorescence was measured two hours after washing out of the media.

The structure of the vesicles could also be observed in electron micrographs generated by negative staining. The nanoparticles in Nanoemulsion BF-200 are spheric, approximately 20 nm in diameter, with an approximately 3 to 4 nm thick bowl and filled with an amorphous material (see FIG. 3 below). Hollow particles were not found.

Investigation of nanoparticles in aminolevulinic acid gel was performed with electron microscopy using freeze-fracture and negative staining techniques.

Figure 5:
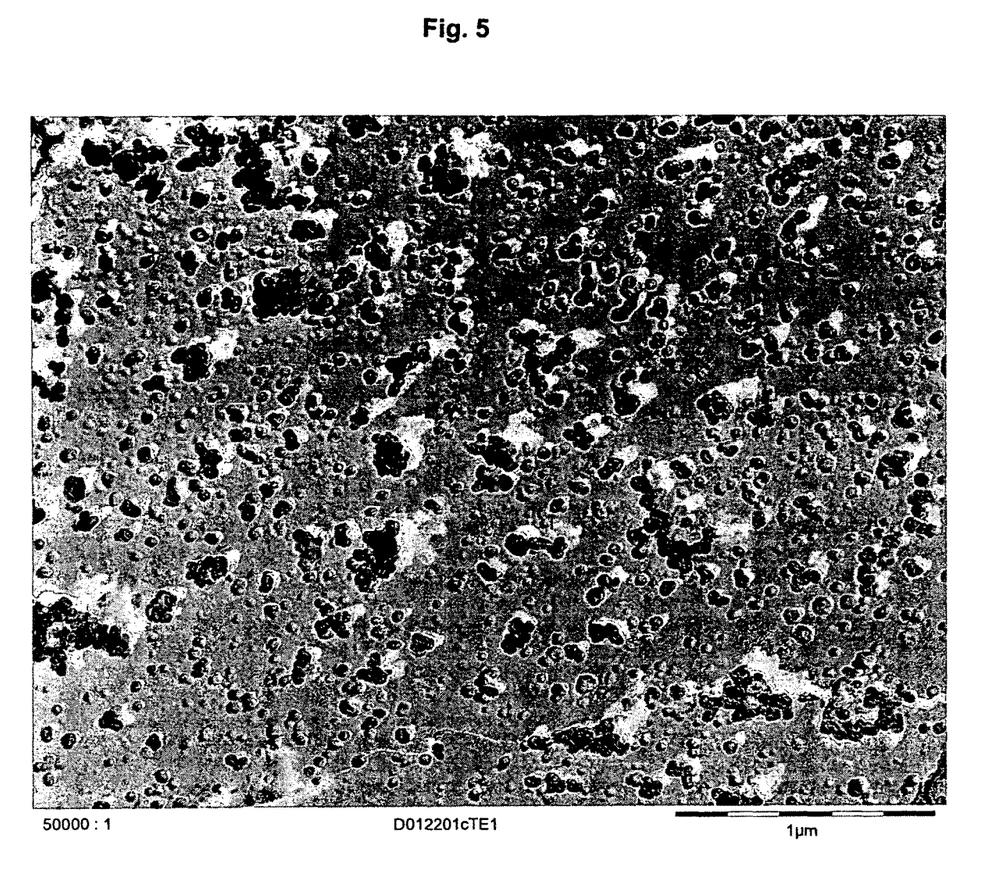
FIG. 5 shows freeze-fracture electron micrographs of aminolevulinic acid gel with a magnification of 50,000 times.

Freeze-fracture electron micrographs of aminolevulinic acid gel confirm that the nanoparticles present in the gel have a size similar to those in the pure Nanoemulsion BF-200. The micrograph illustrates single particles as well as conglomerates (FIG. 5). The morphology and size of the nanoparticles in the gel is not influenced by storage conditions. Examination of BF-200 ALA (10% gel after 4 months storage at 25° C. (60% r.h.) by freeze-fracture electron microscopy revealed particles with similar size and shape than those found in freshly manufactured gel. The planed stability study with the batches of BF-200 ALA gel (10% aminolevulinic acid) and placebo to BF-200 ALA gel to be used in the Phase III clinical study in parallel with the clinical study will include examination of the particle size by electron microscopy at later time points.

Figure 6:
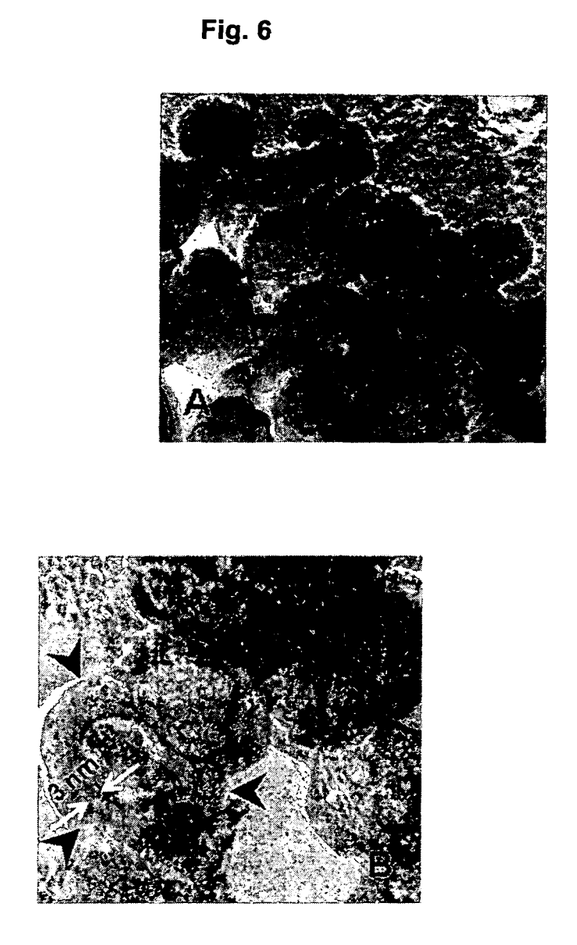
FIG. 6A shows freeze-fracture electron micrographs of aminolevulinic acid gel magnification 250,000 times.
FIG. 6B shows magnification 1,200,000 times.

FIG. 6 shows freeze-fracture electron micrographs of the gel generated with a higher magnification. The fracture surface shows predominantly the envelope of the covered particles. Fracture through the particle itself occurs very rarely. The vesicles seem to be surrounded by a layer of material which is interpreted to represent aminolevulinic acid. This generates a fried-egg-like picture (marked with arrowheads in Part B of FIG. 6).

Electron micrographs produced by negative staining of 10% aminolevulinic acid gel presented nanoparticles with a cloudy diffused surface structure which may confirm the stratification of material on the nanoparticles observed in the freeze-fracture electron micrographs.

Example 4

Absorption into Mammalian Cells: In Vitro Cell Culture Studies about the Uptake of ALA: Cell Culture Studies ALA uptake and conversion to protoporphyrin IX (PpIX) in cultured cells can be monitored by measuring UV-induced PpIX fluorescence. Cell culture experiments were performed with several neoplastic cell lines: HELA, HepG2 and CCD 106 KERTr (a human epithelial keratinocyte cell line). Cells were incubated in aqueous media with Methyl-ALA (MAL), ALA or BF-200 with ALA for a maximum of 3 hours. Under the selected drug concentrations, all three incubation media had a similar pH value. After incubation, cells were washed gently and fresh media were added. PpIX production was measured at different time points by quantifying fluorescence. FIG. 5 shows results obtained for HELA cells.

The effect of increasing concentrations of the nanoemulsion BF-200 (at constant ALA concentration) on PpLX synthesis is shown in FIG. 5. The PpIX fluorescence in the cells was higher with increasing concentration of BF200 and reached a maximum at 3% BF200.

Example 5

The efficacy of nanoemulsion formulation of 5-ALA for the photodynamic therapy of actinic keratosis have been shown in a Phase II dose-finding clinical study started in autumn 2006 and was sponsored by Biofrontera Bioscience GmbH. The placebo-controlled, randomized and double-blind study was conducted in 13 clinical centers in Germany under the medical direction of Prof. Dr. Rolf-Markus Szeimies, University Clinics of Regensburg. Three active doses (1, 3 and 10% ALA) and placebo were used. To verify the efficacy of the compound, 105 patients were treated once by photodynamic therapy with one of three different ALA concentrations or placebo. Patients with 3 to 10 actinic keratosis lesions on the face or on the scalp were included. Each patient received one treatment (1%, 3% or 10% 5-aminolevulinic acid (ALA) or placebo) of all his/her lesions. Red light was applied after 3 hours of incubation. After the treatment session, subjects returned to the clinic after 3 weeks, 8 weeks, and 12 weeks for monitoring the clinical outcome and the healing process. Each time, the investigator assessed the treated actinic keratosis (AK) lesion area for evidence of remaining areas with signs of AK and clinical symptoms. The primary efficacy variable was the total clearance rate of all AK lesions at the week 12 visit, defined as the number of lesions showing complete remission (the lesions have completely cleared and no adherent scaling plaques of AKs are visible any longer). The appearance of pain during the irradiation after BF-200 ALA application was also monitored.

Results: Pre-treatment with 10% ALA preceding PDT was found to be the most effective of the three tested concentrations in clearing AK lesions (statistically significant superior to placebo). When patients were evaluated 12 weeks after a single treatment with BF-200 ALA, at least 60-70% of the treated lesions were completely cured, depending on the weighting of the clinical centers and the area of the head. Clearance rates in the placebo group were about 5-15% of the treated lesions, depending on the weighting of the clinical centers. The clearance rate corresponded well with published results from ALA-PDT studies with similar study design but with higher concentrations of the active substances 5-ALA or Methyl ALA. The cosmetic results were excellent. Only 6% of the patients complained about strong pain. Relevant side effects did not occur during the study, the cosmetic results were excellent. There were no safety concerns regarding any of the four groups during PDT and over a period of 12 weeks after PDT.

As an additional safety measure, this dose-finding part comprised pharmacokinetic assessments. The systemic plasma and urine levels of ALA and its metabolite protoporphyrin IX were measured. The plasma and urine concentrations of these compounds in ALA-treated patients were not increased in comparison to the naturally occurring physiological values in the same individuals.

The invention claimed is:

1. A topical gel composition, the composition comprising:
   3-15% by weight 5-aminolevulinic acid hydrochloride based on the total weight of the composition;
   1-3% by weight xanthan gum based on the total weight of the composition;
   1% to 3% by weight of at least two preservatives, one of the preservatives being propylene glycol based on the total weight of the composition; and
   a nanoemulsion;
   wherein the nanoemulsion is an oil-in-water nanoemulsion comprising:
      50-98% by weight water based on the total weight of the nanoemulsion;
      1-30% by weight surfactant and co-surfactant together wherein the surfactant is soy lecithin and the co-surfactant is polysorbate 80 based on the total weight of the nanoemulsion;
      0.1-15% by weight triglycerides based on the total weight of the nanoemulsion;
      1-2% by weight isopropyl alcohol based on the total weight of the nanoemulsion; and
      5-30 mM phosphate buffer;
   and wherein the nanoemulsion comprises particles with a mean diameter from 5 nm to 35 nm, with a particle size standard deviation from the mean of about 5 nm, prior to incorporation into the topical gel composition.

2. The topical gel composition of claim 1, wherein the amount of 5-aminolevulinic acid hydrochloride is about 10% w/w based on the total weight of the composition.

3. The topical gel composition of claim 1, wherein the amount of nanoemulsion is from about 10% to about 30% w/w based on the total weight of the composition.

4. The topical gel composition of claim 1, wherein the amount of triglycerides in the nanoemulsion is from about 1% to about 8% w/w based on the total weight of the nanoemulsion.

5. The topical gel composition of claim 1, wherein the soy lecithin has a phosphatidylcholine content of at least 90% by weight based on the total weight of the soy lecithin.

6. A topical gel composition, the composition comprising:
   about 10% by weight 5-aminolevulinic acid hydrochloride based on the total weight of the composition;
   1-3% by weight xanthan gum based on the total weight of the composition;
   1% to 3% by weight of at least two preservatives, one of the preservatives being propylene glycol based on the total weight of the composition; and
   a nanoemulsion;
   wherein the nanoemulsion is an oil-in-water nanoemulsion comprising:
      water;
      1-30% by weight surfactant and co-surfactant together wherein the surfactant is soy lecithin and the co-surfactant is polysorbate 80 based on the total weight of the nanoemulsion;
      0.1-15% by weight triglycerides based on the total weight of the nanoemulsion;
      1-2% by weight isopropyl alcohol based on the total weight of the nanoemulsion; and
      5-30 mM phosphate buffer;
   wherein the soy lecithin has a phosphatidylcholine content of at least 90% by weight based on the total weight of the soy lecithin,
   and wherein the nanoemulsion comprises particles with a mean diameter from 5 nm to 35 nm, with a particle size standard deviation from the mean of about 5 nm, prior to incorporation into the topical gel composition.

7. The topical gel composition of claim 6, wherein the amount of 5-aminolevulinic acid hydrochloride is 10% w/w based on the total weight of the composition.

8. The topical gel composition of claim 6, wherein the amount of nanoemulsion is from about 10% to about 30% w/w based on the total weight of the composition.

9. The topical gel composition of claim 6, wherein the amount of triglycerides in the nanoemulsion is from about 1% to about 8% w/w based on the total weight of the nanoemulsion.

10. A topical gel composition, the composition comprising:
    about 10% by weight 5-aminolevulinic acid hydrochloride based on the total weight of the composition;
    2-3% by weight xanthan gum based on the total weight of the composition;
    1% to 3% by weight of at least one preservative wherein the preservative comprises propylene glycol based on the total weight of the composition; and
    a nanoemulsion;
    wherein the nanoemulsion is an oil-in-water nanoemulsion comprising:
       70-95% by weight water based on the total weight of the nanoemulsion;
       about 1% by weight surfactant and co-surfactant together wherein the surfactant is soy lecithin and the co-surfactant is polysorbate 80 based on the total weight of the nanoemulsion;
       0.1-1% by weight triglycerides based on the total weight of the nanoemulsion;
       1-2% by weight isopropyl alcohol based on the total weight of the nanoemulsion; and
       5-30 mM phosphate buffer;
    and wherein the nanoemulsion comprises particles with a mean diameter from 5 nm to 35 nm, with a particle size standard deviation from the mean of about 5 nm, prior to incorporation into the topical gel composition.

* * * * *